United States Patent [19]

Nordin

[11] Patent Number: 4,595,376
[45] Date of Patent: Jun. 17, 1986

[54] MAGAZINE CONTAINING RETENTION PINS FOR THE TREATMENT OF BROKEN AND UNDERMINED TEETH

[76] Inventor: Harald E. Nordin, Villa Amphion, CH-1822 Chernex, Switzerland

[21] Appl. No.: 737,661

[22] Filed: May 24, 1985

[30] Foreign Application Priority Data

May 25, 1984 [EP] European Pat. Off. ......... 84810256.2

[51] Int. Cl.$^4$ ................................................. A61C 5/04
[52] U.S. Cl. ...................................... 433/225; 226/127
[58] Field of Search ........................... 433/225; 226/127

[56] References Cited

U.S. PATENT DOCUMENTS

| | | | |
|---|---|---|---|
| 3,928,915 | 12/1975 | Ellman | 433/225 |
| 4,057,186 | 11/1977 | Hedger | 226/127 |
| 4,155,162 | 5/1979 | Weissman | 433/87 |
| 4,380,433 | 4/1983 | Ellman et al. | 433/225 |

FOREIGN PATENT DOCUMENTS 448621 4/1968 Switzerland .
844644 8/1960 United Kingdom .

*Primary Examiner*—John J. Wilson
*Attorney, Agent, or Firm*—Wender Murase & White

[57] ABSTRACT

A magazine containing a plurality of retention pins for treating broken and undermined teeth which comprises a handle with a head fixed thereto at an obtuse angle. The handle is provided with a device for advancing a bar consisting of a series of retention pins separated by pre-determined breaking point, formed as portion of reduced thickness between pins. The head is provided with a triangularly formed spring for retaining the bar by capturing the portion of reduced thickness between pins. The pins are preferably longitudinally ribbed. The magazine, which acts also as handling tool, facilitates the storage and insertion of retention pins. By providing a plurality of pins in the form of a bar, waste is eliminated.

6 Claims, 6 Drawing Figures

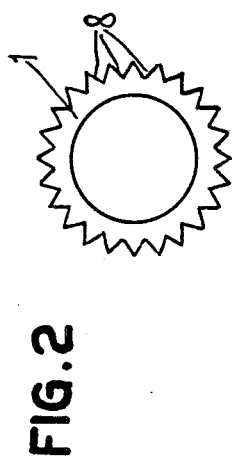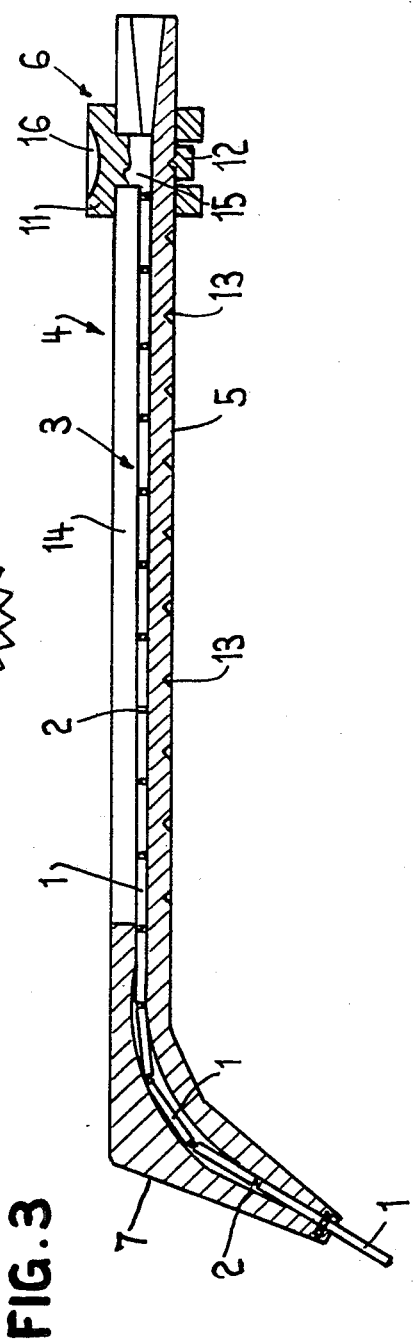
FIG.1
FIG.2
FIG.3

MAGAZINE CONTAINING RETENTION PINS FOR THE TREATMENT OF BROKEN AND UNDERMINED TEETH

BACKGROUND OF THE INVENTION

For many years retention pins have been used for the treatment of broken and undermined teeth, in particular for fixing restorations, for example corners.

Such pins generally have small dimensions, for example a diameter of 0.8 mm and a length of 4–6 mm. Inserting such pins into bores presents problems in handling. In the course of time different instruments, devices and methods have been developed for such insertion. For example, U.S. Pat. No. 4,155,162 discloses a dental anchor magazine in which a single anchor is housed and in which the magazine and anchor include a device for pushing and rotating the anchor whilst inserting it into the tooth. However, with the device described in that patent, a substantial part of the post has to be thrown away after the anchor part has been fixed and broken at a reduced thickness portion of it. Thus the whole magazine is expended for the use of only the part of the post which is used as a retention pin, the rest being wasted. Furthermore, at least the part being inserted is threaded and the other end, which remains, has a right angled manipulating section.

In another insertion method, taught in U.S. Pat. No. 3,928,915, the pins are not screwed in but cemented, for example with a cement for anchoring pins in a tooth for restorations, such as a cement on the base of cyanoacrylate which hardens instantly. Using the teachings of this patent, it is possible to insert several pins at the same time. For procuring a better anchoring, the pins are structured. The fast fixing of the pins allows the use of a strip comprising several pins which are connected together by portions of reduced thickness. However, for handling such strips and inserting pins into a bore in a tooth it is still necessary to use tweezers or similar tools.

SUMMARY OF THE INVENTION

Accordingly, it is an object of the present invention to provide an apparatus which both stores and permits easy manipulation of the retention pins and which utilizes a retention pin without wasting a substantial portion of it.

This object is attained with the present invention by providing a magazine housing having a plurality of retention pins and a device for advancing the pins, the pins being connected together by a portion of reduced thickness thereby forming a bar. The magazine comprises a handle having the pin advancing device secured to it and a head arranged at an obtuse angle with respect to the handle. One function of the head is to retain the retention pins.

BRIEF DESCRIPTION OF THE DRAWING

FIG. 1 illustrates several retention pins according to the invention, which are connected together;

FIG. 2 illustrates, in expanded scale, a section through a retention pin;

FIG. 3 illustrates in longitudinal section, a magazine according to the invention;

DESCRIPTION OF THE PREFERRED EMBODIMENTS

Figure 6:
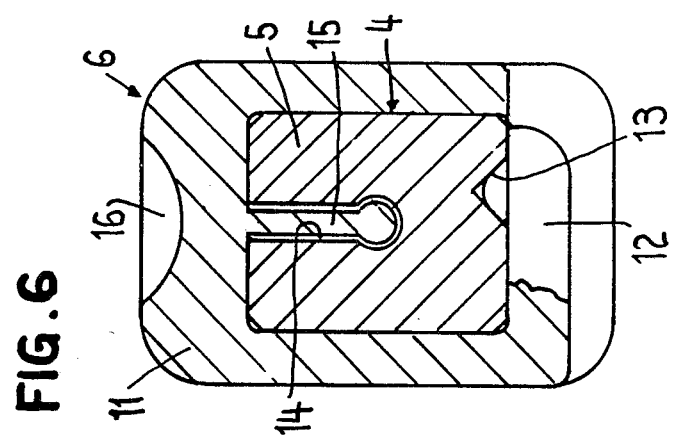
FIG. 6 illustrates, in expanded scale, a section through the back portion of FIG. 3.

FIG. 1 shows a series of retention pins 1, connected by portions of reduced thickness 2, which function as predetermined breaking points. The pins form a bar 3, which can be inserted into a magazine 4. Each retention pin 1 has longitudinal ribbings 8, providing for better anchoring of the pin in the tooth bore in which it has to be fastened.

The magazine 4 consists mainly of a handle 5, a bar advancing device 6 and a head 7. The head is arranged at an obtuse angle relative to the handle for ease of manipulation.

Figure 5:
FIG. 5 illustrates a section of FIG. 4.
Figure 4:
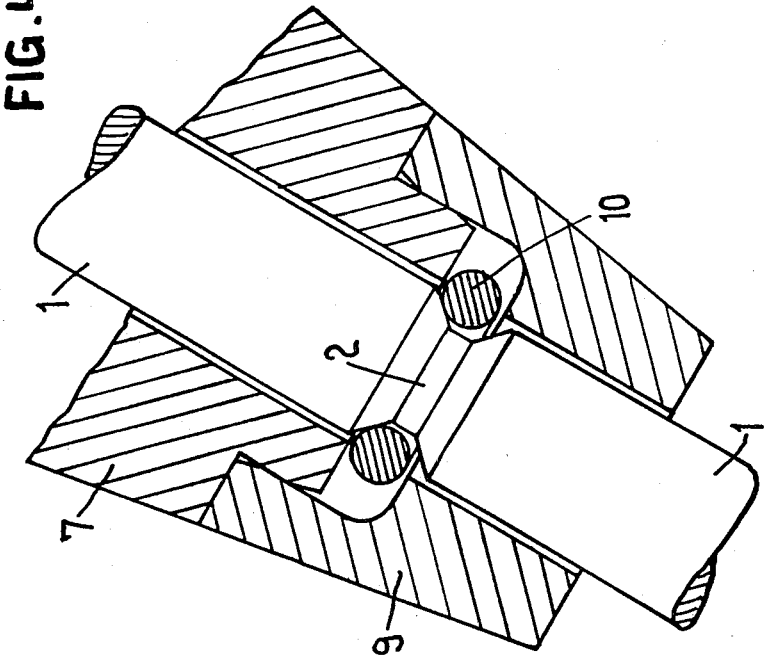
FIG. 4 illustrates, in expanded scale, a detail of FIG. 3.

The construction of the head can best be seen in FIGS. 4 and 5. The head has two parts including a part 9 which encompasses a triangularly formed open spring 10. The portion of the reduced thickness 2 between pins 7 snaps into the spring 10 for latching the pins. The predetermined breaking point 2 is formed as a portion of reduced thickness which conically tapers towards the ends of adjoining pins. While being pushed forward, the bar 3 bends at the predetermined breaking point 2, whereby a fissure may be formed, without breaking the bar wholly through.

The advancing device 6 comprise a slider 11 (see FIG. 6), which encompasses the handle 5 and has a spring part 12 which locks into notches 13 at the lower part of the handle. The distances between notches 13 corresponds to the distance between break points 2. The handle 5 has a slot 14 in which a lug 15 is arranged to glide, the lug preferably being made integrally with the slider 11. The lug 15 is provided with an enlarged end which acts against the end of the bar 3. To facilitate manipulation, the slider 11 can be provided with an indentation 16. For loading a new bar 3, it is necessary to remove the advancing device 6.

The magazine described above represents a preferred simple embodiment and variations from this embodiment are possible within the scope of the invention. For example, the point of the head 7 may be provided with a gripping mechanism other than the triangular open spring 10, for example, a gripping mechanism similar to that commonly used in lead pencil holders. The bar advancing means can also be realized in a manner similar to that used in pencil holders.

Usually, the magazine is made of a plastic material with a head and a point made of metal. It is possible to produce the handle and the slider together with the bar of retention pins and to pack it hygienically clean for dental use, and fasten it to the head. Both parts, the handle and the head, can be provided with threads or can be fastened by a bayonet joint or the like.

The retention pins are preferably made of titanium and are fixed by a fast hardening cement into bores of a tooth. One such cement which may be used is ethyl cyano-acrylate.

What I claim:

1. A magazine for housing a plurality of retention pins for the treatment of broken or undermined teeth, said retention pins being arranged in the form of a bar and separated by pre-determined break points between successive retention pins, said magazine having means for advancing said bar and a handle, said handle having said bar advancing means fixed thereto and a head fixed thereto at an obtuse angle, said head including a means for retaining said retention pins.

2. The magazine according to claim 1, wherein said handle has notches separated by a distance corresponding to the distance between consecutive break points and a slot, and wherein the bar advancing means comprises a slider which encompasses the handle and which has a spring part; said spring part being adapted to lock onto said notches, and wherein said slider has a lug adapted to glide in said slot in the handle.

3. The magazine according to claim 1, wherein said means for retaining the retention pins comprises a triangularly formed open spring operable to snap into a break point, said break points comprising portions of reduced thickness between adjacent pins, and wherein said head is made of two parts.

4. The magazine according to claim 1, wherein the handle and the bar advancing means are fabricated as a unit, adapted to be plugged onto the head.

5. The magazine according to claim 1, wherein said retention pins are provided with longitudinal ribbings.

6. The magazine according to claim 1, wherein said retention pins are made of titanium.

* * * * *